United States Patent
Zhang et al.

(10) Patent No.: US 12,116,334 B1
(45) Date of Patent: Oct. 15, 2024

(54) METHOD FOR OLEFIN HYDROFORMYLATION USING IRIDIUM-BASED CATALYST

(71) Applicant: NANJING INSTITUTE OF MICROINTERFACE TECHNOLOGY CO., LTD, Jiangsu (CN)

(72) Inventors: Zhibing Zhang, Jiangsu (CN); Xingbang Hu, Jiangsu (CN); Chenfei Yao, Jiangsu (CN); Zheng Zhou, Jiangsu (CN); Lei Li, Jiangsu (CN)

(73) Assignee: NANJING INSTITUTE OF MICROINTERFACE TECHNOLOGY CO., LTD, Nanjing (CN)

( * ) Notice: Subject to any disclaimer, the term of this patent is extended or adjusted under 35 U.S.C. 154(b) by 0 days.

(21) Appl. No.: 18/705,067

(22) PCT Filed: Nov. 16, 2021

(86) PCT No.: PCT/CN2021/130914
§ 371 (c)(1),
(2) Date: Apr. 26, 2024

(87) PCT Pub. No.: WO2023/070761
PCT Pub. Date: May 4, 2023

(30) Foreign Application Priority Data

Oct. 27, 2021 (CN) .......... 202111256879.2

(51) Int. Cl.
*C07C 27/16* (2006.01)
(52) U.S. Cl.
CPC .......... *C07C 27/16* (2013.01); *C07C 2531/22* (2013.01)
(58) Field of Classification Search
CPC ..... C07C 27/16; C07C 2531/22; C07C 45/50; C07C 47/02
See application file for complete search history.

(56) References Cited

FOREIGN PATENT DOCUMENTS

| CN | 1222903 A | 7/1999 |
| CN | 103180278 A | 6/2013 |
| CN | 106140302 A | 11/2016 |
| CN | 111484437 A | 8/2020 |

OTHER PUBLICATIONS

Fox et al., a model iridium hydroformylation system with the large bite angle ligand xantphos: reactivity with parahydrogen and implications for hydroformylation catalysis, (Inorganic Chemistry, vol. 45, No. 18, 2006).*

* cited by examiner

*Primary Examiner* — Jafar F Parsa
(74) *Attorney, Agent, or Firm* — Chun-Ming Shih; LANWAY IPR SERVICES

(57) ABSTRACT

Provided in the present invention is an iridium-based catalyst, which is characterized in that the chemical structural formula of the iridium-based catalyst is:

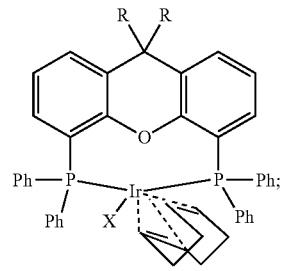

wherein Ph is a phenyl, R is a methyl or an ethyl, and X is one or more of $CH_3CO_2$, $NO_3$, Cl, $BF_4$, $PF_6$ and $SbF_6$. In the present invention, a rhodium-based catalyst in the prior art is replaced with the iridium-based catalyst, such that the reaction cost is reduced, and the yield of reactants is increased.

11 Claims, 1 Drawing Sheet

METHOD FOR OLEFIN HYDROFORMYLATION USING IRIDIUM-BASED CATALYST

FIELD OF THE INVENTION

The present invention relates to the field of aldehyde reactions, and in particular to an iridium-based catalyst, a preparation method therefor, and a aldehyde method.

BACKGROUND OF THE INVENTION

Butyraldehyde and octanol are very widely used bulk chemical raw materials. At present, the industrial synthesis of butyl-octanol is mainly through the olefin hydroformylation reaction to produce n-butyraldehyde and iso-butyraldehyde, which are then used as raw materials for subsequent reactions. The olefin hydroformylation reaction is a key step in the synthesis of butyl-octanol.

So far, there have been many patents on the olefin hydroformylation to synthesize n-butyraldehyde and iso-butyraldehyde. These patents and current industrial methods generally use rhodium-based catalysts. For example, patents WO0200583, EP3712126A1, and CN102826967A use triphenylphosphorus-rhodium as the catalyst: the patent JP2002047294 uses cyclooctadiene acetate-rhodium as the catalyst: the patent CN110156580 uses 6,6'-((3,3'-di-tert-butyl-5,5'-dimethoxy-[1,1'-biphenyl]-2, bis(oxy))dibenzo[d,f] [1,3,2] dioxaphosphocyclopentane Alkene-rhodium as the catalyst: the patent CN103896748A uses acetylmorpholine-rhodium as the catalyst: the patent EP3770144A1 uses acetate-rhodium as the catalyst: the patent CN111348995A uses tris[2,4-di-tert-butylphenyl] phosphite-rhodium as the catalyst: the patent U.S. Pat. No. 9,550,179 uses long Chain carboxylic acid-rhodium as the catalyst: the patent CN102826973A uses acetylacetone carbonyl-rhodium as the catalyst: the patent EP2417094B1 uses triphenylphosphine carbonyl rhodium hydride as the catalyst; the patent EP2417093B1 uses dipolyrhodium acetate+triphenylphosphine trisulfonate sodium salt as the catalyst.

In addition to the above patents, rhodium-based catalysts are also commonly used in published papers. For example, Angew: Chem. Int. Ed. 2019, 58, 2120-2124 used heterocyclic phosphorus ligand-rhodium as the catalyst, and the obtained highest n-butyraldehyde/iso-butyraldehyde ratio is 2.6; ACS Catal. 2018, 8, 5799-5809 used N-Triphos ligand-rhodium as the catalyst, the obtained highest n-butyraldehyde/iso-butyraldehyde ratio is 2.3; Journal of Molecular Catalysis A: Chemical, 2009, 300, 116-120 used triphenylphosphorus carbonyl rhodium hydride as the catalyst, and the obtained highest n-butyraldehyde/iso-butyraldehyde ratio is 12.7; Chem. Eur. J. 2017, 23, 14769-14777 used porphyrin-modified triphenylphosphorus ligand-rhodium as the catalyst, the obtained highest n-butyraldehyde/iso-butyraldehyde ratio is 2.3.

Although rhodium metal can be recycled many times in olefin hydroformylation reactions. Slow loss and deactivation during the reaction process are inevitable. Due to the rapid increase in international rhodium metal prices, the cost of catalysts in the corresponding process has also increased rapidly. Secondly, the low n-butyraldehyde/iso-butyraldehyde ratio causes the production process to produce a large amount of low-value iso-butyraldehyde.

In view of this, the present invention is proposed.

SUMMARY OF THE INVENTION

A first objective of the present invention is to provide an iridium-based catalyst. Compared with the existing rhodium-based catalyst, the iridium-based catalyst used in the present invention is cheaper and greatly reduces the production cost.

A second objective of the present invention is to provide a preparation method of an iridium-based catalyst, which has mild reaction conditions, can significantly reduce energy consumption, and the obtained iridium-based catalyst has better catalytic effects than previous catalysts.

A third objective of the present invention is to provide a method for olefin hydroformylation with an iridium-based catalyst. Through using the above iridium-based catalyst in the method for olefin hydroformylation of the present invention, not only the reaction temperature is low and reaction conditions are mild, but the selectivity of the target product is also greatly improved.

In order to achieve the above objectives of the present invention, the following technical schemes are adopted.

The present invention provides an iridium-based catalyst. The chemical structure formula of the iridium-based catalyst is:

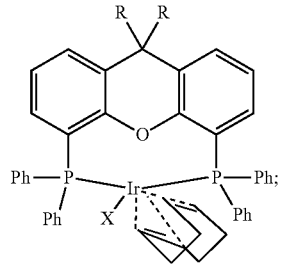

wherein Ph is a phenyl, R is a methyl or an ethyl, and X is one or more of $CH_3CO_2$, $NO_3$, Cl, $BF_4$, $PF_6$ and $SbF_6$. The Chinese name of the iridium-based catalyst is 4,5-bis(diphenylphosphorus)-9,9-dialkylxanthene-iridium catalyst, abbreviated as POP(R)—Ir—X.

The present invention also provides a preparation method of the iridium-based catalyst, which includes the following steps:

mixing and stirring 4,5-bis(diphenylphosphoryl)-9,9-dimethylxanthene, solvent and iridium compound, and then heating and stirring to obtain the iridium-based catalyst.

A tetraoxofuran is selected as the solvent, and a cyclooctadiene iridium chloride is selected as the iridium compound. The 4,5-Bis(diphenylphosphoryl)-9,9-dimethylxanthene and cyclooctadiene iridium chloride are reacted in tetrahydrofuran at a molar ratio of 2:1 to obtain the iridium-based catalyst POP(R)—Ir—X.

Preferably, a time for mixing and stirring 4,5-bis(diphenylphosphoryl)-9,9-dimethylxanthene, solvent and iridium compound is 1.5 h-3 h, preferably 2 h.

Preferably, during the heating and stirring process, a temperature is raised to 40-60° C., preferably 50° C., and then stirring for 1.5 h-3 h, preferably 2 h:

Preferably, when X in the iridium-based catalyst is $CH_3CO_2$, $NO_3$, Cl, $BF_4$, $PF_6$ or $SbF_6$, the temperature is first raised and stirred to obtain a substance to be substituted, and then a compound containing an X-based group is added to replace the substance to be substituted.

The present invention also provides a method for olefin hydroformylation using an iridium-based catalyst, which includes the following steps:

under a condition that the iridium-based catalyst is existed, olefins, carbon monoxide, and hydrogen are used as raw materials to perform a catalytic reaction.

Before the reaction, the catalyst needs to be dissolved in n-butyraldehyde, iso-butyraldehyde, toluene or tetraxofuran.

Preferably, the reaction temperature of the catalytic reaction is 70-120° C., preferably 80-110° C.

Preferably, the catalytic reaction time is 6-9 h, preferably 8 h. The reaction time does not need to be too long, and a higher yield rate of the target product can be obtained in a shorter reaction time.

Preferably, a reaction pressure of the catalytic reaction is 0.5 Mpa~3.0 Mp, preferably between 1.0 Mpa~2.0 Mpa.

Preferably, a partial pressure ratio of the olefin to the carbon monoxide is 10:1-1:10, preferably 5:1-1:5.

Preferably, a partial pressure ratio of the olefin to the hydrogen is 10:1-1:10, preferably 5:1-1:5.

Preferably, a mass of the iridium-based catalyst is 0.005 wt %-2.0 wt % of a mass of the solvent, preferably 0.05 wt %-1.0 wt %.

The present invention uses an iridium-based catalyst and uses propylene, carbon monoxide and hydrogen as raw materials to perform a hydroformylation reaction to prepare n-butyraldehyde and iso-butyraldehyde. Compared with the existing rhodium-based catalyst, the flow loss and deactivation of rhodium metal during the reaction is inevitable, which will inevitably affect the conversion rate and selectivity of the reaction, and the price of rhodium metal is also rising rapidly.

The iridium-based catalyst used in the present invention is cheap, has mild preparation conditions and hydroformylation reaction conditions, and has better effects in producing n-butyraldehyde and iso-butyraldehyde.

BRIEF DESCRIPTION OF THE DRAWINGS

Various other advantages and benefits will become apparent to those of ordinary skill in the art upon reading the following detailed description of the preferred embodiments. The drawings are for the purpose of illustrating preferred embodiments only and are not to be construed as limiting the present invention. Also, throughout the drawings, the same reference characters are used to designate the same components. In the drawings.

DESCRIPTION OF THE PREFERRED EMBODIMENTS

Figure 1:
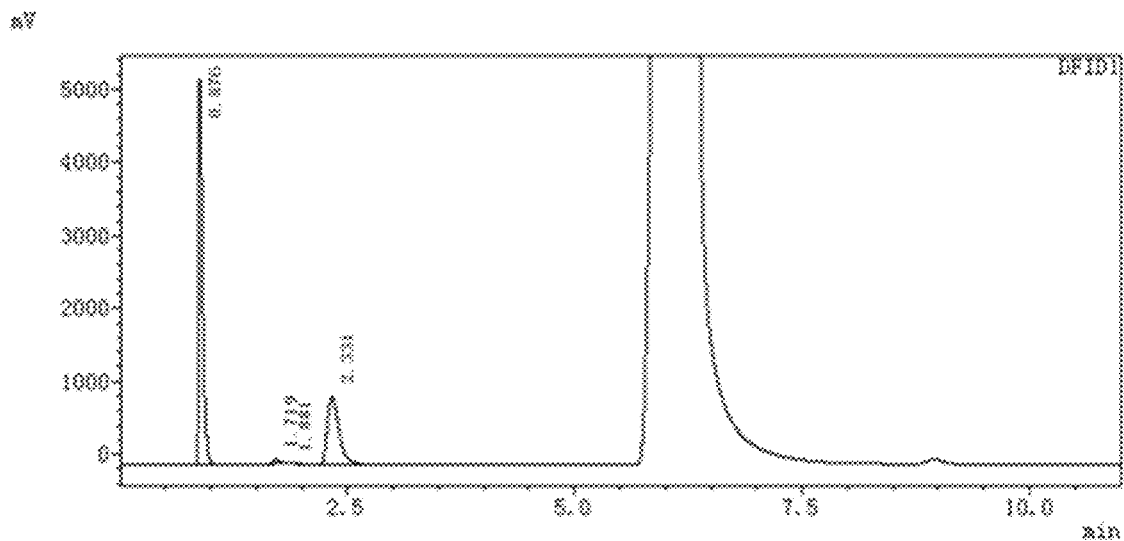
FIG. 1 is a chromatogram of the reaction product in Embodiment 6 of the present invention.
Figure 2:
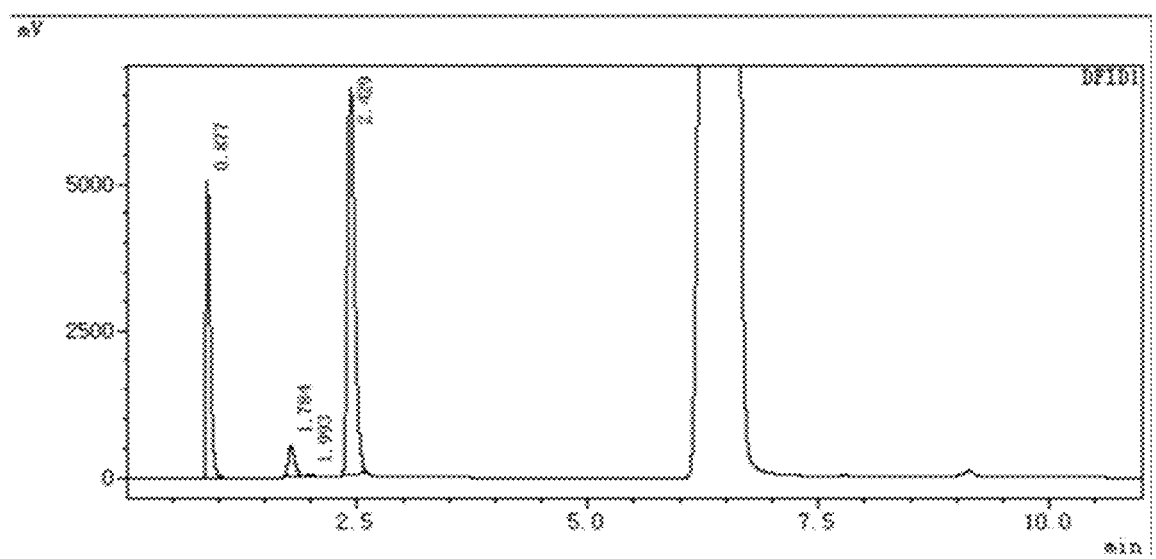
FIG. 2 is a chromatogram of the reaction product in Embodiment 10 of the present invention.

The schemes of the present invention will be described in detail below with reference to embodiments, however, those skilled in the art will understand that the following embodiments are only used to illustrate the present invention and should not be regarded as limiting the scope of the present invention. If the specific conditions are not specified in the embodiments, the conditions should be carried out according to the conventional conditions or the conditions recommended by the manufacturer. If the manufacturer of the reagents or instruments used is not indicated, they are all conventional products that can be purchased commercially.

Embodiment 1

The preparation method of iridium-based catalyst is as follows:

Synthesis of POP($CH_3$)—Ir—Cl: under nitrogen protection, 100 ml of tetrahydrofuran, 5.0 g of cyclooctadiene iridium chloride, and 8.6 g of 4,5-bis(diphenylphosphonyl)-9,9-dimethylxanthene are added into a 250 ml reaction bottle. Stirring and reacting at room temperature for 2 hours, and then raising the temperature to 50° C., and stirring and reacting for 2 hours. The solvent is evaporated to dryness, and the obtained solid is washed twice with 20 ml of n-hexane and dried to obtain 11.9 g of POP($CH_3$)—Ir—Cl.

Embodiment 2

The specific operating steps are the same as those in Embodiment 1. The differences between them are that the mixing and stirring time is 1.5 h, the heating and stirring temperature is 40° C., and the stirring time is 1.5 h. Finally, 11.4 g of POP($CH_3$)—Ir—Cl is obtained.

Embodiment 3

The specific operating steps are the same as those in Embodiment 1. The differences between them are that the mixing and stirring time is 3 h, the heating and stirring temperature is 60° C., and the stirring time is 3 h. Finally, 11.5 g of POP($CH_3$)—Ir—Cl is obtained.

Embodiment 4

Synthesis of POP($CH_3$)—Ir—$NO_3$: 150 ml of tetrahydrofuran, 5.0 g of POP($CH_3$)—Ir—Cl prepared in Embodiments 1-3, 0.92 g of silver nitrate, and 20 ml of water are added into a 250 ml reaction bottle. Stirring and reacting at room temperature in the dark for 6 hours, and then the insoluble matter is filtered off. The solvent is evaporated to dryness, and the obtained solid is washed twice with 20 ml of n-hexane and dried to obtain 4.5 g of POP($CH_3$)—Ir—$NO_3$.

Embodiment 5

Synthesis of POP($CH_3$)—Ir—$CH_3CO_2$: 150 ml of tetrahydrofuran, 5.0 g of POP($CH_3$)—Ir—Cl prepared in Embodiments 1-3, 0.90 g of silver acetate, and 20 ml of water are added into a 250 ml reaction bottle. Stirring and reacting at room temperature in the dark for 6 hours, and then the insoluble matter is filtered off. The solvent is evaporated to dryness, and the obtained solid is washed twice with 20 ml of n-hexane and dried to obtain 4.6 g of POP($CH_3$)—Ir—$CH_3CO_2$.

Embodiment 6

The operating steps of the aldehyde reaction are as follows:

The 81 mg of POP($CH_3$)—Ir—$CH_3CO_2$ obtained from Embodiment 5 and 12 ml of toluene are added into a 50 ml high-pressure reaction kettle. After replacing it with hydrogen for three times, 3 bar of propylene, 8 bar of carbon monoxide, and 8 bar of hydrogen are added in sequence, and then the temperature is raised to 90° C. with stirring. Stirring and reacting it at this temperature for 8 hours, and the reaction solution is cooled to 0° C. After slowly releasing the pressure, samples are taken for gas chromatography analysis. According to the gas phase results, it can be calculated that the catalyst conversion number TON is 78.8, and the selectivity of n-butyraldehyde and iso-butyraldehyde is 99.8% (n-butyraldehyde/iso-butyraldehyde=29.1:1).

Embodiments 7-11

The propylene hydroformylation reaction method of Embodiment 6 is adopted while changing different temperatures to carry out the reaction, and the results are shown in Table 1.

TABLE 1

Effects of temperature on propylene hydroformylation reaction.

| Embodiment | Temperature (° C.) | Catalyst conversion number TON | Selectivity of n-butyraldehyde and iso-butyraldehyde (%) | n-butyraldehyde/ iso-butyraldehyde |
|---|---|---|---|---|
| 7 | 70 | 29.6 | 99.8 | 19.8:1 |
| 8 | 80 | 51.1 | 99.7 | 23.1:1 |
| 9 | 100 | 123.6 | 99.5 | 16.9:1 |
| 10 | 110 | 162.1 | 99.6 | 14.3:1 |
| 11 | 120 | 192.7 | 99.5 | 12.0:1 |

Embodiments 12-17

The propylene hydroformylation reaction method of Embodiment 6 is adopted while changing the pressure of gas, and the results are shown in Table 2.

TABLE 2

Effects of pressure on propylene hydroformylation reaction.

| Embodiment | Reaction pressure (MPa) | Propylene (bar) | CO (bar) | $H_2$ (bar) | Catalyst conversion number TON | Selectivity of n-butyraldehyde and iso-butyraldehyde (%) | n-butyraldehyde/ iso-butyraldehyde |
|---|---|---|---|---|---|---|---|
| 12 | 0.5 | 3 | 1 | 1 | 35.3 | 99.5 | 26.1:1 |
| 13 | 1.0 | 2 | 4 | 4 | 53.5 | 99.6 | 26.7:1 |
| 14 | 2.2 | 2 | 10 | 10 | 110.9 | 99.5 | 22.5:1 |
| 15 | 1.4 | 10 | 2 | 2 | 36.6 | 99.7 | 26.5:1 |
| 16 | 2.0 | 10 | 5 | 5 | 93.1 | 99.5 | 23.2:1 |
| 17 | 3.0 | 14 | 8 | 8 | 50.1 | 99.3 | 22.4:1 |

Comparative Example 1

Other operating steps are the same as those in Embodiment 6, and the differences between them are that: the catalyst used is tris[2,4-di-tert-butylphenyl] phosphite-rhodium disclosed in the patent CN111348995A. The results are as follows:

TABLE 3

Effects of different catalysts on hydroformylation reaction.

| | Catalyst conversion number TON | Selectivity of n-butyraldehyde and iso-butyraldehyde (%) | n-butyraldehyde/ iso-butyraldehyde |
|---|---|---|---|
| Embodiment 6 | 78.8 | 99.8 | 29.1:1 |
| Comparative Example 1 | 60.2 | 98.5 | 25.4:1 |

As can be seen from the above tables that: during the process of using the iridium-based catalyst for hydroformylation reaction, the hydroformylation reaction is best when the temperature is 80° C. and the propylene gas pressure is 3 bar, and the present invention obtains the highest n-butyraldehyde/iso-butyraldehyde ratio of 29.1:1. This shows that the present invention still has good reaction selectivity and reaction conversion rate under low temperature and low pressure conditions. By comparing with the rhodium-based catalyst of Comparative Example 1, it can be known that the new catalyst of the present invention not only reduces the cost, but also has better catalytic effect than the traditional catalyst.

Therefore, the present invention adopts a new iridium-based catalyst to conduct the catalytic reaction and explores the reaction conditions, thereby realizing the reaction under the conditions of low energy consumption and good reaction efficiency.

Finally, it should be noted that the above embodiments are merely used to illustrate the technical schemes of the present invention, rather than to limit the present invention. Although the present invention has been described in detail with reference to the above-mentioned embodiments, those of ordinary skill in the art should understand that they can still modify the technical schemes recorded in the above-mentioned embodiments or make equivalent substitutions for some or all of the technical features. However, these modifications or substitutions do not cause the essence of the corresponding technical scheme to depart from the scope of the technical scheme of each embodiment of the present invention.

What is claimed is:
1. A method for olefin hydroformylation using an iridium-based catalyst, comprising the following steps:
   under a condition that the iridium-based catalyst is existed, olefins, carbon monoxide, and hydrogen are used as raw materials to perform a catalytic reaction;
   before the catalytic reaction, the iridium-based catalyst is dissolved in a solvent;
   the solvent is one of n-butyraldehyde, iso-butyraldehyde, toluene or tetraxofuran;
   characterized in that a chemical structural formula of the iridium-based catalyst is:

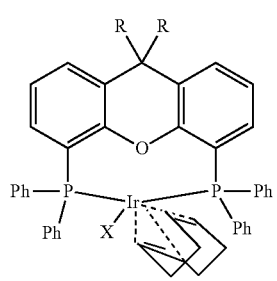

wherein Ph is a phenyl, R is a methyl or an ethyl, and X is one or more of $CH_3CO_2$, $NO_3$, $BF_4$, $PF_6$ and $SbF_6$;
wherein a preparation method of the iridium-based catalyst comprises the following steps:
   mixing and stirring 4,5-bis(diphenylphosphoryl)-9,9-dimethylxanthene, solvent and iridium compound, and then heating and stirring to obtain the iridium-based catalyst;

wherein a time for mixing and stirring 4,5-bis(diphenylphosphoryl)-9,9-dimethylxanthene, solvent and iridium compound is 2 h;

wherein during the heating and stirring process, a temperature is raised to 50° C., and then stirring for 2 h;

when X in the iridium-based catalyst is $CH_3CO_2$, $NO_3$, $BF_4$, $PF_6$ or $SbF_6$, the temperature is first raised and stirred to obtain a substance to be substituted, and then a compound containing an X-based group is added to replace the substance to be substituted.

2. The method for olefin hydroformylation according to claim 1, wherein a reaction temperature of the catalytic reaction is between 70~120° C.

3. The method for olefin hydroformylation according to claim 1, wherein a reaction temperature of the catalytic reaction is between 80° C.~110° C.

4. The method for olefin hydroformylation according to claim 1, wherein a reaction pressure of the catalytic reaction is 0.5 Mpa~3.0 Mpa.

5. The method for olefin hydroformylation according to claim 1, wherein a reaction pressure of the catalytic reaction is between 1.0 Mpa~2.0 Mpa.

6. The method for olefin hydroformylation according to claim 1, wherein a partial pressure ratio of the olefin to the carbon monoxide is 10:1-1:10.

7. The method for olefin hydroformylation according to claim 1, wherein a partial pressure ratio of the olefin to the carbon monoxide is 5:1-1:5.

8. The method for olefin hydroformylation according to claim 1, wherein a partial pressure ratio of the olefin to the hydrogen is 10:1-1:10.

9. The method for olefin hydroformylation according to claim 1, wherein a partial pressure ratio of the olefin to the hydrogen is 5:1-1:5.

10. The method for olefin hydroformylation according to claim 1, where a mass of the iridium-based catalyst is 0.005 wt %-2.0 wt % of a mass of the solvent.

11. The method for olefin hydroformylation according to claim 1, where a mass of the iridium-based catalyst is 0.05 wt %-1.0 wt % of a mass of the solvent.

* * * * *